(12) United States Patent
Li et al.

(10) Patent No.: US 12,121,507 B2
(45) Date of Patent: *Oct. 22, 2024

(54) WATER-SOLUBLE CURCUMIN LIQUID AND PREPARATION METHOD AND APPLICATION THEREOF

(71) Applicants: Honglong Li, Luohe (CN); Xiaosong Xu, Luohe (CN); Ziheng Jin, Luohe (CN); Linzheng Li, Luohe (CN); Congying Shi, Luohe (CN); Yulian Guo, Luohe (CN); Chunfeng Yu, Luohe (CN); Yaqiong Zhang, Luohe (CN)

(72) Inventors: Honglong Li, Luohe (CN); Xiaosong Xu, Luohe (CN); Ziheng Jin, Luohe (CN); Linzheng Li, Luohe (CN); Congying Shi, Luohe (CN); Yulian Guo, Luohe (CN); Chunfeng Yu, Luohe (CN); Yaqiong Zhang, Luohe (CN)

(73) Assignee: HENAN ZHONGDA HENGYUAN BIOTECHNOLOGY STOCK CO., LTD., Luohe (CN)

( * ) Notice: Subject to any disclaimer, the term of this patent is extended or adjusted under 35 U.S.C. 154(b) by 472 days.

This patent is subject to a terminal disclaimer.

(21) Appl. No.: 17/473,967

(22) Filed: Sep. 13, 2021

(65) Prior Publication Data
US 2022/0347156 A1 Nov. 3, 2022

(30) Foreign Application Priority Data
Apr. 30, 2021 (CN) .......................... 202110484524.2

(51) Int. Cl.
| | | |
|---|---|---|
| A61K 31/375 | (2006.01) | |
| A23L 2/56 | (2006.01) | |
| A23L 2/58 | (2006.01) | |
| A23L 27/10 | (2016.01) | |
| A23L 29/10 | (2016.01) | |
| A23L 33/105 | (2016.01) | |
| A23L 33/15 | (2016.01) | |
| A23L 35/00 | (2016.01) | |
| A61K 9/107 | (2006.01) | |
| A61K 31/12 | (2006.01) | |
| A61K 47/22 | (2006.01) | |

(52) U.S. Cl.
CPC .............. *A61K 31/375* (2013.01); *A23L 2/56* (2013.01); *A23L 2/58* (2013.01); *A23L 27/10* (2016.08); *A23L 29/10* (2016.08); *A23L 33/105* (2016.08); *A23L 33/15* (2016.08); *A23L 35/10* (2016.08); *A61K 9/107* (2013.01); *A61K 31/12* (2013.01); *A61K 47/22* (2013.01); *A23V 2002/00* (2013.01)

(58) Field of Classification Search
CPC ...... A61K 9/107; A61K 31/12; A61K 31/375; A61K 47/22; A23L 2/56; A23L 2/58; A23L 27/10; A23L 29/10; A23L 33/105; A23L 33/15; A23L 35/10; A23L 29/25; A23L 29/35; A23L 2/52; A23L 5/43; A23V 2002/00
See application file for complete search history.

(56) References Cited

FOREIGN PATENT DOCUMENTS

| | | |
|---|---|---|
| CN | 104922105 A | 9/2015 |
| CN | 109846865 A | 6/2019 |

OTHER PUBLICATIONS

Jidnyasa Pantwalawalkar, Harinath More, Deu Bhange, Udaykumar Patil, Namdeo Jadhav, "Novel curcumin ascorbic acid cocrystal for improved solubility", Journal of Drug Delivery Science and Technology, vol. 61, 2021, 102233, (Year: 2021).*

* cited by examiner

*Primary Examiner* — Robert H Havlin
*Assistant Examiner* — Pierre Paul Eleniste

(57) ABSTRACT

A method for preparing a water-soluble curcumin liquid includes the following steps: A) dissolving curcumin, vitamin C and ascorbyl palmitate in an ethanol aqueous solution, evaporating ethanol under reduced pressure, and vacuum drying to obtain a curcumin-vitamin C-ascorbyl palmitate co-crystal; and B) high-speed emulsifying the curcumin-vitamin C-ascorbyl palmitate co-crystal and a water-soluble colloidal solution that includes an emulsifying additive under vacuum, sequentially conducting a two-stage wet grinding, a homogenization and a potential adjustment to obtain the water-soluble curcumin liquid.

9 Claims, 1 Drawing Sheet

WATER-SOLUBLE CURCUMIN LIQUID AND PREPARATION METHOD AND APPLICATION THEREOF

Curcumin extract is obtained by extracting, refining, crystallizing and drying the dried roots of perennial herbaceous ginger (Curcuma longa L.). The main ingredients of the extract are curcumin, demethoxycurcumin, and bisdemethoxycurcumin. Curcumin has good coloring ability. As one of the raw materials of condiments, it has a long history of consumption in China, South Asia and Southeast Asia. Curcumin is easily soluble in ethanol, acetic acid, and propylene glycol. It is basically insoluble in water. It has good heat resistance, but it is sensitive to light, easily degraded and faded in light environment, sensitive to pH, and easy to crystallize and precipitate under acidic condition. The application of curcumin is largely limited.

TECHNICAL FIELD

The invention related to food technology, and a water-soluble curcumin liquid and a preparation method and application thereof.

BACKGROUND TECHNIQUE

Curcumin extract is obtained by extracting, refining, crystallizing and drying the dried roots of perennial herbaceous ginger (Curcuma longa L.). The main ingredient of the extract is curcumin, monodemethylation, oxycurcumin, and double demethoxycurcumin. Curcumin has good coloring ability. As one of the raw materials of condiments, it has a long history of consumption in China, South Asia and Southeast Asia. Curcumin is easily soluble in ethanol, acetic acid, and propylene glycol. It is basically insoluble in water. It has good heat resistance, but it is sensitive to light, easily degraded and faded in light environment, sensitive to pH, and easy to crystallize and precipitate under acidic condition. The application of curcumin is largely limited.

In addition, as traditional Chinese medicine, curcumin has good health effects. Modern medical research has confirmed that curcumin has good anti-inflammatory, antioxidant, free radical scavenging, tumor suppression, cardiovascular protection and other pharmacological effects. However, in practical applications, curcumin is poorly water-soluble and cannot be absorbed well by the body, which results in that its good physiological functions cannot be effectively exerted. Therefore, there is a need to improve the solubility of curcumin in water and enhance the absorption.

There are patents on how to improve the solubility of curcumin and the preparation of curcumin preparations with different requirements. For example, CN 104922105A discloses a method for preparing curcumin preparations with synthetic emulsifiers, such as Tween and polyglycerol esters to emulsify curcumin. CN 109846865A discloses a curcumin preparation and its preparation method, using n-hexane, ethanol, ethyl acetate solvent to dissolve curcumin, phospholipids, and cyclodextrin. The use of a large amount of organic solvents increase safety risks, and solvent residues in subsequent products cannot ensure the quality, safety and application of curcumin preparations.

SUMMARY OF THE INVENTION

In view of these, the technical problem to be solved by the present invention is to provide a water-soluble curcumin liquid and its preparation method and application. The preparation method provided by the present invention does not require synthetic emulsifiers and is solvent-free in the preparation process. The obtained curcumin liquid has excellent water solubility, the light resistance has been greatly improved, and the acid precipitation resistance has also been significantly improved.

In one embodiment, the present invention provides a method for preparing a water-soluble curcumin liquid. The method includes the following steps:

A) dissolving curcumin, vitamin C and ascorbyl palmitate in an ethanol aqueous solution, evaporating ethanol under reduced pressure, and vacuum drying to obtain a curcumin-vitamin C (VC)-ascorbyl palmitate co-crystal; and B) high-speed emulsifying the curcumin-vitamin C-ascorbyl palmitate co-crystal and a water-soluble colloidal solution that includes an emulsifying additive under vacuum, sequentially conducting a two-stage wet grinding, a homogenization and a Zeta potential adjustment to obtain the water-soluble curcumin liquid.

In another embodiment, a mass ratio of curcumin, vitamin C and ascorbyl palmitate is 100:(0.001–30):(0.001–30).

In another embodiment, in step A), curcumin, vitamin C, ascorbyl palmitate and ethanol dissolution are heated at 0-60° C.; ethanol is evaporated under a pressure of 0.05 MPa to 1.0 MPa and at 25° C. to 100° C.

In another embodiment, in the water-soluble colloidal solution, the emulsifying additive is lactitol, glycerin, propylene glycol, erythritol, maltitol, sorbitol, or a combination thereof; the water-soluble colloidal solution includes a water-soluble colloidal that is selected from the group consisting of sodium starch octenyl succinate, arabic gum, ghatti gum, xanthan gum, pullulan, maltodextrin, microcrystalline cellulose, a-cyclodextrin, P-cyclodextrin, y-ring dextrin, and a combination thereof; and the water-soluble colloid solution has an emulsifying additive concentration of 1 wt % to 90 wt % and a water-soluble colloid concentration of 1 wt % to 50 wt %.

In another embodiment, the two-stage wet grinding includes a first grinding and a second grinding; the first grinding uses zirconia beads with diameter of 0.6 mm-0.8 mm and is conducted at a speed of 500 rpm to 3500 rpm for 1 to 10 hours; and the second grinding uses zirconia beads with diameter of 0.2 mm-0.3 mm and is conducted at a speed of 500 rpm to 3500 rpm for 1 to 10 hours.

In another embodiment, the homogenization is conducted under 90 MPa-200 MPa, preferably, 100 MPa-170 MPa.

In another embodiment, the potential adjustment uses a Zeta potential modifier selected from the group consisting of sodium hexametaphosphate, sodium polyphosphate, sodium pyrophosphate, sodium tripolyphosphate and a combination thereof, and a colloidal emulsion potential is adjusted to −10 mv to −60 mv, preferably, −30 mv to −50 mv.

In another embodiment, the water-soluble curcumin liquid has a curcumin-vitamin C-ascorbyl palmitate co-crystal concentration of 0.01 wt % to 70 wt %.

In another embodiment, the present application provides a water-soluble curcumin liquid prepared by the method of the present application.

In another embodiment, the present application provides an application of the water-soluble curcumin liquid prepared by the method of the present application in food.

DETAILED DESCRIPTION

Figure 1:
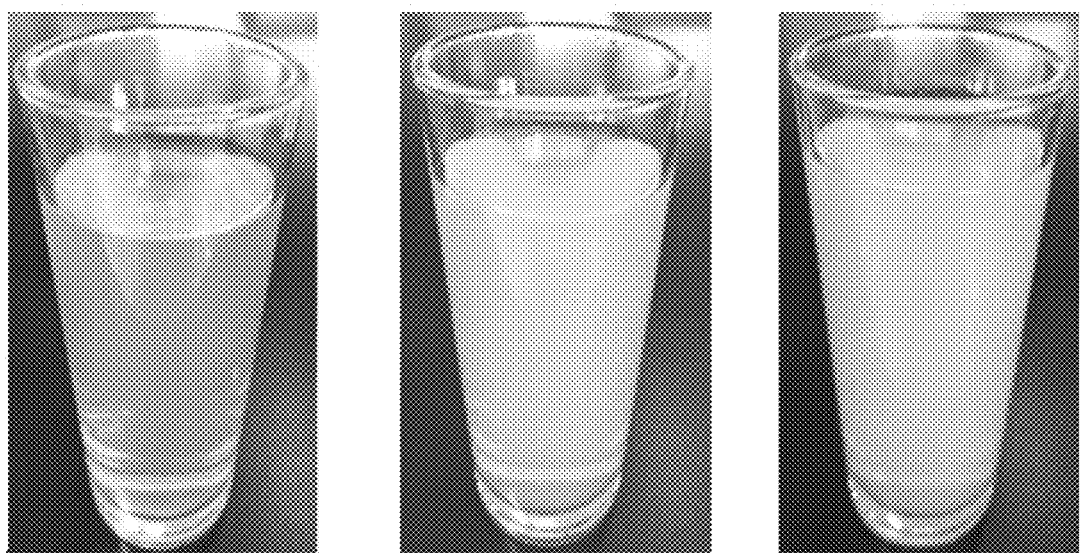
FIG. 1 is a photo showing the solubility of the water-soluble curcumin liquid of Example 1 in water.

The present invention has the following beneficial effects:
1. The present invention obtains a water-soluble curcumin liquid with uniform quality and stable emulsion state. This product has excellent water solubility, and has significantly improved light resistance and acid precipitation resistance;
2. The present invention forms a co-crystal of VC, ascorbyl palmitate and curcumin, which can effectively protect curcumin and reduce the oxidative degradation of curcumin. At the same time, the curcumin-VC-ascorbyl palmitate co-crystal can promote the combination of curcumin, colloid, and emulsifiers to improve the water solubility of curcumin;
3. The present invention discloses a preparation method of turmeric preparation without synthetic emulsifier and solvent-free in the preparation process. The product obtained does not have the problems of quality safety and application completeness, and the preparation process is safer, which is suitable to the industrial production of the product;
4. The present invention uses an effective combination of vacuum emulsification technology, two-stage wet grinding, and ultra-high pressure homogenization technology, which can significantly reduce the particle size of curcumin and improve the water solubility of curcumin.

In order to further understand the present invention, the liquid water-soluble curcumin provided by the present invention and its preparation method are described below in conjunction with examples. The protection scope of the present invention is not limited by the following examples.

EXAMPLE 1

Weighing 120 g of 93% curcumin, dissolving it in 1200 g of 95% ethanol under stirring, slowly adding 1.2 g of VC and 1.2 g of ascorbyl palmitate, and slowly heating the mixture to 35° C. to 40° C., slowly stirring until completely dissolved. The temperature of the mixture was heated to 65° C. to 75° C., and ethanol was evaporated under a vacuum of 0.08 MPa to obtain a dark yellow viscous substance. The viscous substance was transferred to a vacuum drying oven and dried for 15 hours in an environment of 0.09 MPa and 75° C. to 80° C. The solvent residue was detected to be <50 ppm to obtain a VC-ascorbyl palmitate-curcumin co-crystal.

Weighing 110 g of arabic gum, 10 g of a-cyclodextrin, and 200 g of glycerin, and dissolving them in 216 g of deionized water to prepare a water-soluble colloidal solution A with a concentration of 60% by weight. Weighing 65.5 g of VC-ascorbyl palmitate-curcumin co-crystal, adding it to the water-soluble colloidal solution A, keeping the material at 35° C. to 40° C., and emulsifying for 60 minutes under emulsification tank vacuum of 0.085 MPa. The curcumin was uniformly dispersed and the fluidity was good. Curcumin emulsion B was obtained.

Putting the curcumin emulsion B into a wet grinding equipment for a first grinding. The grinding medium was 0.6 mm-0.8 mm zirconia beads. Grinding at 1300 rpm for 4 hours until the particle size D90 was less than 1.0 um. Then carrying out a second grinding. The grinding medium was 0.2 mm-0.3 mm zirconia beads, and the grinding was carried out at 1,000 rpm for 4 hours until the particle size D90 was less than or equal to 0.3 um, and curcumin emulsion C was obtained. The curcumin emulsion C was subjected to ultra-high pressure homogenization under a pressure of 130 MPa to obtain a uniform and stable curcumin emulsion D. Preparing 5% sodium hexametaphosphate solution with deionized water, adjusting the Zeta potential of curcumin emulsion D to −38 mv, and obtaining a water-soluble curcumin liquid.

The testing showed that the water-soluble curcumin liquid had excellent water solubility. The curcumin content was 10.2%, and the D90 particle size was 278 nm.

FIG. 1 shows the solubility of the water-soluble curcumin liquid of Example 1 in water.

EXAMPLE 2

Weighing 150 g of 93% curcumin, dissolving it in 1700 g of 95% ethanol under stirring, slowly adding 1.8 g of VC and 2.0 g of ascorbyl palmitate, and slowly heating the mixture to 35° C. to 40° C., slowly stirring until completely dissolved. The temperature of the mixture was heated to 65° C. to 75° C., and ethanol was evaporated under a vacuum of 0.08 MPa to obtain a dark yellow viscous substance. The viscous substance was transferred to a vacuum drying oven and dried for 13 hours in an environment of 0.09 MPa and 75° C. to 80° C. The solvent residue was detected to be <50 ppm to obtain a VC-ascorbyl palmitate-curcumin co-crystal.

Weighing 80 g of sodium starch octenyl succinate, 10 g of ghatti gum, 50 g of sorbitol, and 200 g of glycerin, and dissolving them in 286 g of deionized water to prepare a water-soluble colloidal solution A with a concentration of 54% by weight. Weighing 37 g of VC-ascorbyl palmitate-curcumin co-crystal, adding it to the water-soluble colloidal solution A, keeping the material at 35° C. to 40° C., and emulsifying for 45 minutes under emulsification tank vacuum of 0.085 MPa. The curcumin was uniformly dispersed and the fluidity was good. Curcumin emulsion B was obtained.

Putting the curcumin emulsion B into a wet grinding equipment for a first grinding. The grinding medium was 0.6 mm-0.8 mm zirconia beads. Grinding at 1200 rpm for 5 hours until the particle size D90 was less than 1.0 um. Then carrying out a second grinding. The grinding medium was 0.2 mm-0.3 mm zirconia beads, and the grinding was carried out at 1,000 rpm for 2.5 hours until the particle size D90 was less than or equal to 0.3 um, and curcumin emulsion C was obtained. The curcumin emulsion C was subjected to ultra-high pressure homogenization under a pressure of 140 MPa to obtain a uniform and stable curcumin emulsion D. Preparing 5% sodium hexametaphosphate solution with deionized water, adjusting the Zeta potential of curcumin emulsion D to −38 mv, and obtaining a water-soluble curcumin liquid.

The testing showed that the water-soluble curcumin liquid had excellent water solubility. The curcumin content was 5.2%, and the D90 particle size was 262 nm.

Comparative Example 1

Curcumin Raw Materials

Figure 2:
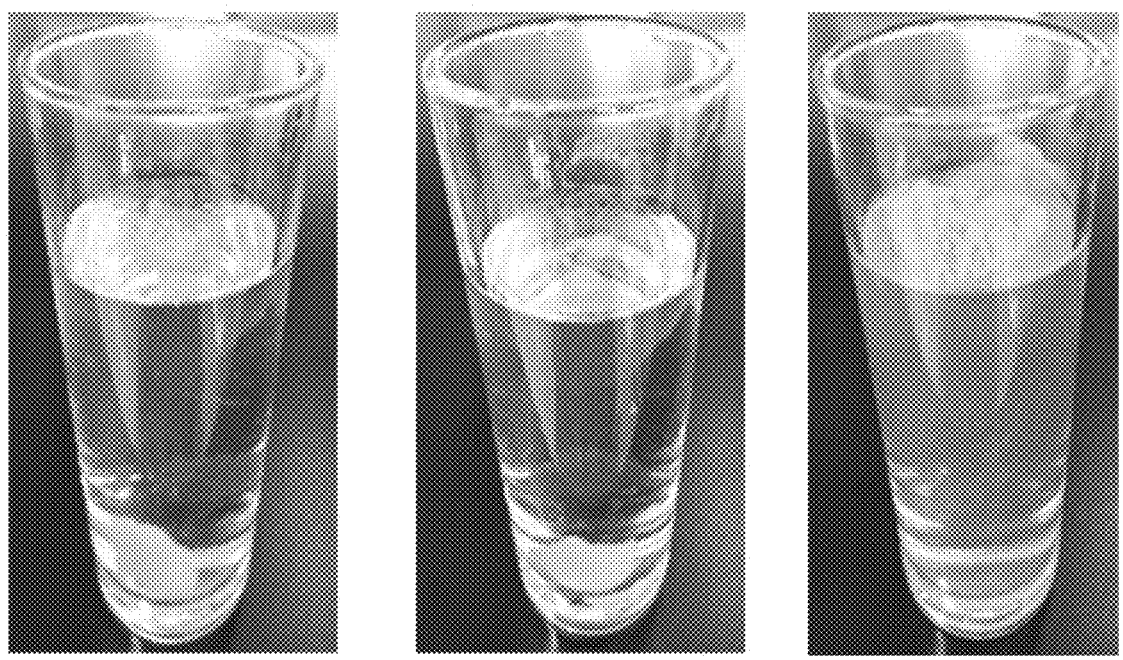
FIG. 2 is a photo showing the solubility of the curcumin raw material of Comparative Example 1 in water.

The curcumin raw material was dispersed in water, and the result is shown in FIG. 2. FIG. 2 is a photo of solubility of the curcumin raw material in water. It can be seen from FIG. 2 that curcumin is insoluble in water.

Comparative Example 2

The preparation was carried with the same process as Example 1, except that the curcumin emulsion D was not adjusted for Zeta potential. The process and results are as follows:

Weighing 120 g of 93% curcumin, dissolving it in 1200 g of 95% ethanol under stirring, slowly adding 1.2 g of VC and 1.2 g of ascorbyl palmitate, and slowly heating the mixture to 35° C. to 40° C., slowly stirring until completely dissolved. The temperature of the mixture was heated to 65° C. to 75° C., and ethanol was evaporated under a vacuum of 0.08 MPa to obtain a dark yellow viscous substance. The viscous substance was transferred to a vacuum drying oven and dried for 15 hours in an environment of 0.09 MPa and 75° C. to 80° C. The solvent residue was detected to be <50 ppm to obtain a VC-ascorbyl palmitate-curcumin co-crystal.

Weighing 110 g of arabic gum, 10 g of a-cyclodextrin, and 200 g of glycerin, and dissolving them in 216 g of deionized water to prepare a water-soluble colloidal solution A with a concentration of 60% by weight. Weighing 65.5 g of VC-ascorbyl palmitate-curcumin co-crystal, adding it to the water-soluble colloidal solution A, keeping the material at 35° C. to 40° C., and emulsifying for 60 minutes under emulsification tank vacuum of 0.085 MPa. The curcumin was uniformly dispersed and the fluidity was good. Curcumin emulsion B was obtained.

Putting the curcumin emulsion B into a wet grinding equipment for a first grinding. The grinding medium was 0.6 mm-0.8 mm zirconia beads. Grinding at 1300 rpm for 4 hours until the particle size D90 was less than 1.0 um. Then carrying out a second grinding. The grinding medium was 0.2 mm-0.3 mm zirconia beads, and the grinding was carried out at 1,000 rpm for 4 hours until the particle size D90 was less than or equal to 0.3 um, and curcumin emulsion C was obtained. The curcumin emulsion C was subjected to ultra-high pressure homogenization under a pressure of 130 MPa to obtain a uniform and stable curcumin emulsion D.

After testing, the curcumin emulsion D had excellent water solubility, the curcumin content was 10.2%, and the D90 particle size was 312 nm. After the sample was placed in an environment of 30° C. for 7 days, the curcumin emulsion D showed signs of layering. The upper and lower curcumin content and particle size are shown in Table 1:

TABLE 1

|  | Curcumin content/wt % | D90/nm |
|---|---|---|
| Upper layer | 9.98% | 282 |
| Lower layer | 10.67% | 386 |

EXAMPLE 3

1. Light Stability Testing
100 ppm Solutions were Prepared Using

The water-soluble curcumin liquid of Example 1 was dissolved in deionized water with a pH value of 4.0 to 4.5 to prepare a 100 pm solution. The water-soluble curcumin liquid of Example 2 was dissolved in deionized water with a pH value of 4.0 to 4.5 to prepare a 200 pm solution. The solutions were placed in PET bottles in an environmental simulation box (37° C., 21000 lux illumination, 75% humidity), illuminated for 7 days. The absorbance value of the solution was measured every 24 hours, and the rate of change of the absorbance value was calculated. The results are shown in Table 2 and Table 3.

TABLE 2

Light Stability of Example 1

|  | 0 day | 1 day | 2 days | 3 days | 4 days | 5 days | 7 days |
|---|---|---|---|---|---|---|---|
| Absorbance | 1.125 | 1.112 | 1.078 | 1.001 | 0.982 | 0.978 | 0.955 |
| Loss % | 0 | 1.16% | 4.18% | 11.02% | 12.71% | 13.07% | 15.1% |

TABLE 3

Light Stability of Example 2

|  | 0 day | 1 day | 2 days | 3 days | 4 days | 5 days | 7 days |
|---|---|---|---|---|---|---|---|
| Absorbance | 1.276 | 1.252 | 1.191 | 1.128 | 1.119 | 1.087 | 1.026 |
| Loss % | 0 | 1.88% | 6.66% | 11.6% | 12.3% | 14.8% | 19.6% |

The water-soluble curcumin liquid of Example 2 had a total loss rate of 48.78%

2. Acid Stability Test 2000 pm solutions were prepared using deionized water with a pH value of 3.2 to 3.5, and placed in 300 mL PET bottles. The solutions were stored at room temperature, the precipitation at the bottom of the PET bottles was recorded every 48 hours. The results are shown in Table 4.

TABLE 4

Acid Stability of Examples 1-2 and Comparative Example 1

| Precipitation | 0 day | 2 days | 4 days | 6 days | 8 days | 10 days | 15 das |
|---|---|---|---|---|---|---|---|
| Ex. 1 | No | No | No | No | + | + | + |
| Ex. 2 | No | No | No | No | + | + | ++ |
| Comp. Ex. 2 | + | ++ | +++ | ++++ | ++++ | ++++ | ++++ |

Note:
"+" indicates precipitation,
"++" more precipitation,
"+++" most precipitation The above are only the preferred embodiments of the present invention. It should be pointed out that for those of ordinary skill in the art, without departing from the principle of the present invention, several improvements and modifications can be made, and these improvements and modifications are also It should be regarded as the protection scope of the present invention.

The invention claimed is:

1. A method for preparing a water-soluble curcumin liquid, comprising the following steps:
   A) dissolving curcumin, vitamin C and ascorbyl palmitate in an ethanol aqueous solution, evaporating ethanol under reduced pressure, and vacuum drying to obtain a curcumin-vitamin C-ascorbyl palmitate co-crystal; and
   B) high-speed emulsifying the curcumin-vitamin C-ascorbyl palmitate co-crystal and a water-soluble colloidal solution that includes an emulsifying additive under vacuum, sequentially conducting a two-stage wet grinding, a homogenization and a Zeta potential adjustment to obtain the water-soluble curcumin liquid.

2. The method according to claim 1, wherein a mass ratio of curcumin, vitamin C and ascorbyl palmitate is 100: (0.001-30):(0.001-30).

3. The method according to claim 1, wherein in step A), curcumin, vitamin C, ascorbyl palmitate and ethanol aqueous solution are heated at 0-60° C.; ethanol is evaporated under a pressure of 0.05 MPa to 1.0 MPa and at 25° C. to 100° C.

4. The method according to claim 1, wherein
   in the water-soluble colloidal solution, the emulsifying additive is lactitol, glycerin, propylene glycol, erythritol, maltitol, sorbitol, or a combination thereof;
   the water-soluble colloidal solution comprises a water-soluble colloidal that is selected from the group consisting of sodium starch octenyl succinate, arabic gum, ghatti gum, xanthan gum, pullulan, maltodextrin, microcrystalline cellulose, α-cyclodextrin, β-cyclodextrin, γ-ring dextrin, and a combination thereof; and
   the water-soluble colloid solution has an emulsifying additive concentration of 1 wt % to 90 wt % and a water-soluble colloid concentration of 1 wt % to 50 wt %.

5. The method according to claim 1, wherein the two-stage wet grinding comprises a first grinding and a second grinding; the first grinding uses zirconia beads with diameter of 0.6 mm-0.8 mm and is conducted at a speed of 500 rpm to 3500 rpm for 1 to 10 hours; and the second grinding uses zirconia beads with diameter of 0.2 mm-0.3 mm and is conducted at a speed of 500 rpm to 3500 rpm for 1 to 10 hours.

6. The method according to claim 1, wherein the homogenization is conducted under 90 MPa-200 MPa.

7. The method according to claim 1, wherein the potential adjustment uses a Zeta potential modifier selected from the group consisting of sodium hexametaphosphate, sodium polyphosphate, sodium pyrophosphate, sodium tripolyphosphate and a combination thereof, and a colloidal emulsion potential is adjusted to −10 mv to −60 mv.

8. The method according to claim 1, wherein the water-soluble curcumin liquid has a curcumin-vitamin C-ascorbyl palmitate co-crystal concentration of 0.01 wt % to 70 wt %.

9. A water-soluble curcumin liquid prepared by the method according to claim 1.

\* \* \* \* \*